United States Patent
Dunn

(10) Patent No.: US 11,160,768 B2
(45) Date of Patent: Nov. 2, 2021

(54) PARAFFIN WAX WITH CBD ISOLATE

(71) Applicant: Edmund M. Dunn, Bala Cynwyd, PA (US)

(72) Inventor: Edmund M. Dunn, Bala Cynwyd, PA (US)

(*) Notice: Subject to any disclaimer, the term of this patent is extended or adjusted under 35 U.S.C. 154(b) by 0 days.

(21) Appl. No.: 16/660,007

(22) Filed: Oct. 22, 2019

(65) Prior Publication Data

US 2021/0113488 A1    Apr. 22, 2021

(51) Int. Cl.
| | | |
|---|---|---|
| *A61K 31/05* | (2006.01) | |
| *A61K 47/06* | (2006.01) | |
| *A61K 9/00* | (2006.01) | |
| *A61K 36/886* | (2006.01) | |
| *A61K 47/44* | (2017.01) | |

(52) U.S. Cl.
CPC ............ *A61K 31/05* (2013.01); *A61K 9/0014* (2013.01); *A61K 36/886* (2013.01); *A61K 47/06* (2013.01); *A61K 47/44* (2013.01)

(58) Field of Classification Search
None
See application file for complete search history.

(56) References Cited

U.S. PATENT DOCUMENTS

| 8,846,409 B2 | 9/2014 | Flockhart et al. |
| 10,226,496 B2 | 3/2019 | Sekura et al. |
| 2018/0207213 A1 | 7/2018 | McElvany |
| 2019/0142788 A1 | 5/2019 | Hossain |

FOREIGN PATENT DOCUMENTS

| WO | 2018175796 A1 | 9/2018 |
| WO | 2019056123 A1 | 3/2019 |
| WO | 2019136351 A1 | 7/2019 |

OTHER PUBLICATIONS

Journal of the American College of Toxicology, 4, Chapter 3, pp. 65-106. (Year: 1985).*
Mutual Beauty Antibacterial Paraffin Wax (Amazon.ca). (Year: 2016).*
Merrick, M., Chapter 8, Therapeutic Modalities as an Adjunct to Rehabilitation from Physical Rehabilitation of the Injured Athlete, Eds. Andrews, J., Harrelson, G., and Wilk, K. p. 123. (Year: 2012).*
Kiefer, D., Integrative Medicine Alert, vol. 20, iss. 12. (Year: 2017).*
Candlewic Aloe Vera Spa Wax and Anita review (Amazon.com). (Year: 2017).*
Beautyland, Pure Cannabis Paraffin Treatment, https://www.beautyland.uk/post/2017/11/01/untitled. (Year: 2017).*
Spruce Natural Labs, takespruce.com/product/topical-cbd-cream/?rfsn=2642977.36ce4, Topical CBD Cream, accessed Jul. 19, 2019, Raleigh, North Carolina.
Total Beauty Experience, totalbeautyexp.com/collections/cbd-daily/products/intensive-cream-8-oz, CBD Daily Intensive Cream, accessed Jul. 19, 2019, Sacramento, California.

* cited by examiner

*Primary Examiner* — Michael Barker
(74) *Attorney, Agent, or Firm* — BakerHostetler

(57) ABSTRACT

The method comprising melting a composition of matter comprising paraffin wax, mineral oil, aloe vera and CBD, placing a body member into said melted composition several times, withdrawing the body member from said composition, allowing the composition to solidify on the body member and peeling the solidified composition from said body member, said composition being solid, non-tacky, non-sticky and essentially non-material depositing at room temperature.

2 Claims, 6 Drawing Sheets

PARAFFIN WAX WITH CBD ISOLATE

FIELD OF INVENTION

This invention relates to the heat treatment of the skin of body members using compositions containing CBD.

BACKGROUND OF INVENTION

Various methods and therapeutic uses of cannabidiol are known.

U.S. Pat. App. Pub. No. 2018/0207213 discloses an antiviral pharmaceutical topical lip balm, lip gloss, vaginal cream, gel, ointment, foam or jelly containing cannabidiol (CBD), mineral oil, lanolin, aloe-barbadensis extract, paraffin wax and coloring agents. Paraffin wax is disclosed as a thickening agent to provide a lip stick for manual application at room temperature.

WO 2018/175,796 A1 and WO 2019/136,351 A1 disclose topical CBD-containing formulations along with the other components at varying percent concentrations. WO 2018/175,796 A1 discloses various creams, ointments and the like based predominantly on tetrahydrocannabinoic acid and cannabidiolic acid which are applied topically. WO 2019/136,351 A1 discloses personal care formulations containing cannabidoids for administration in the form of wipes, containers, tubes, sachets, patches, pumps and sticks as shampoos, mousse, lotions, creams, salves and ointments.

Spruce Natural Labs, Raleigh, N.C., Topical CBD Cream discloses a topical CBD skin cream on the market composed of ½% wt %, CBD, together with water, mineral oil, petrolatum, glycerin, microcrystalline wax, lanolin alcohol, paraffin, panthenol, magnesium sulfate, decyl oleate, octyldodecanol, aluminum stearates, fragrance, citric acid, magnesium stearate, methylchloroisothiazolinone and methylisothiazolinone. Concentrations of the latter compounds are not disclosed.

Sekura, et. al. U.S. Pat. No. 10,226,496 B2 discloses a topical formulation, containing extract of *Cannabis sativa* or *cannabis* indica and at least one other component from the group consisting of benzoyl peroxide, oxybenzone, octocrylene, octyl methoxycinnamate, ethylhexyl salicylate, and avobenzone, the formulation being a lotion, cream, ointment, liniment, tonic, nasal spray, soap, shampoo, lip balm or sunscreen.

Hossain, U.S. Pat. App. Pub. No. 2019/0142788 and Wong, et. al., WO 2019/056123 A1 disclose a topical composition containing a cannabinoid in a carrier which is caprylocapial polyoxy-8-glycarides, poloxamer 407, lecithin and isopropyl palmitate.

The slab of this invention is normally relatively rigid at normal room temperature. It has a self-sustaining physical shape, normally in the form of a slab in the preferred commercial size measuring approximately 10.5 inches in length, 3.75 inches in width and 0.5 inches in thickness.

SUMMARY OF THE INVENTION

The composition of matter of the present invention comprises the following.

The composition of matter comprising paraffin wax, mineral oil, aloe vera and CBD, said composition being solid, non-tacky, non-sticky and essentially non-material depositing at room temperature.

The preferred composition of matter comprising paraffin wax 91.57%, mineral oil 7.875%, aloe vera (1x decolorized) 0.04762%, lanolin USA (extra decolorized) 0.2632%, fragrance 0.2381%, CBD (isolate less than 0.3% THC) 0.0007326% and benzethonium chloride USP 0.007326%, said composition being solid, non-tacky, non-sticky and essentially non-material depositing at room temperature. All percentages are by weight Each of the above percentages are subject to variation in the range of 1 to 10%, and preferably 1 to 5% by weight.

The method comprising melting a composition of matter comprising paraffin wax, mineral oil, aloe vera and CBD, said composition being solid, non-tacky, non-sticky and essentially non-material depositing at room temperature, placing a body member into said melted composition, withdrawing the body member from said composition, allowing the composition to solidify on the body member and peeling the solidified composition from said body member.

The preferred method comprising melting a composition comprising paraffin wax 91.57%, mineral oil 7.875%, aloe vera (1x decolorized) 0.04762%, lanolin USA (extra decolorized) 0.2632%, fragrance 0.2381%, CBD (isolate less than 0.3% THC) 0.0007326% and benzethonium chloride USP 0.007326%, said composition being solid, non-tacky, non-sticky and non-material depositing at room temperature, placing a body member into said melted composition several times, withdrawing the body member from said composition, allowing the composition to solidify on the body member and peeling the solidified composition from said body member, the percentage being variable as stated above.

Usages

Medical

The present invention is useful in the treatment of soreness, joint stiffness and pain, rheumatism, arthritis, basic aches and pains related to ankle, elbow, hand and feet. This invention provides a method of treating, preventing or ameliorating both chronic or acute pain, comprising applying any one of the compositions described herein at elevated temperature, to the skin of a subject in need thereof to provide the concurrent benefits of CBD and warming.

Beauty and Wellness

The present invention is also useful in the treatment as a pore cleanser, skin exfoliate, skin rejuvenator and moisturizer.

Composition

The composition of this invention is solid at room temperature and comprises:

Paraffin Wax (Kosher Grade): 90%

Mineral Oil (Kosher Grande): 8%

Aloe Vera, Lanolin, Color (Dye), Fragrance and CBD: 2%

Total: 100%

In the solid state at or around room temperature, the composition can be manually handled without leaving a significant deposit on the skin of the body part of the user.

THE DRAWINGS

Turning to the drawings.

DESCRIPTION OF THE PREFERRED EMBODIMENTS

Figure 1:
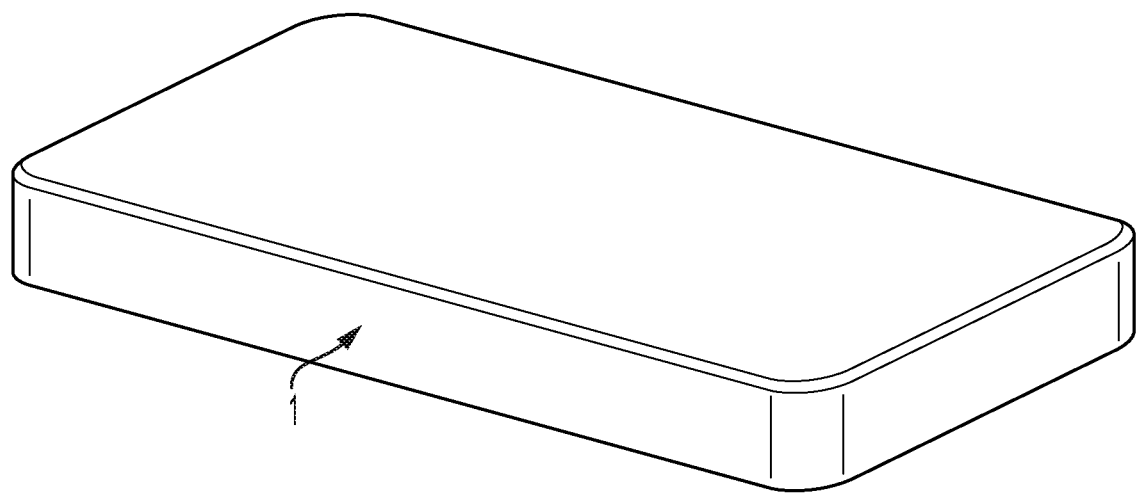
FIG. 1 shows the composition of the invention in the form of a solid slab at or around room temperature without packaging.
Figure 2:
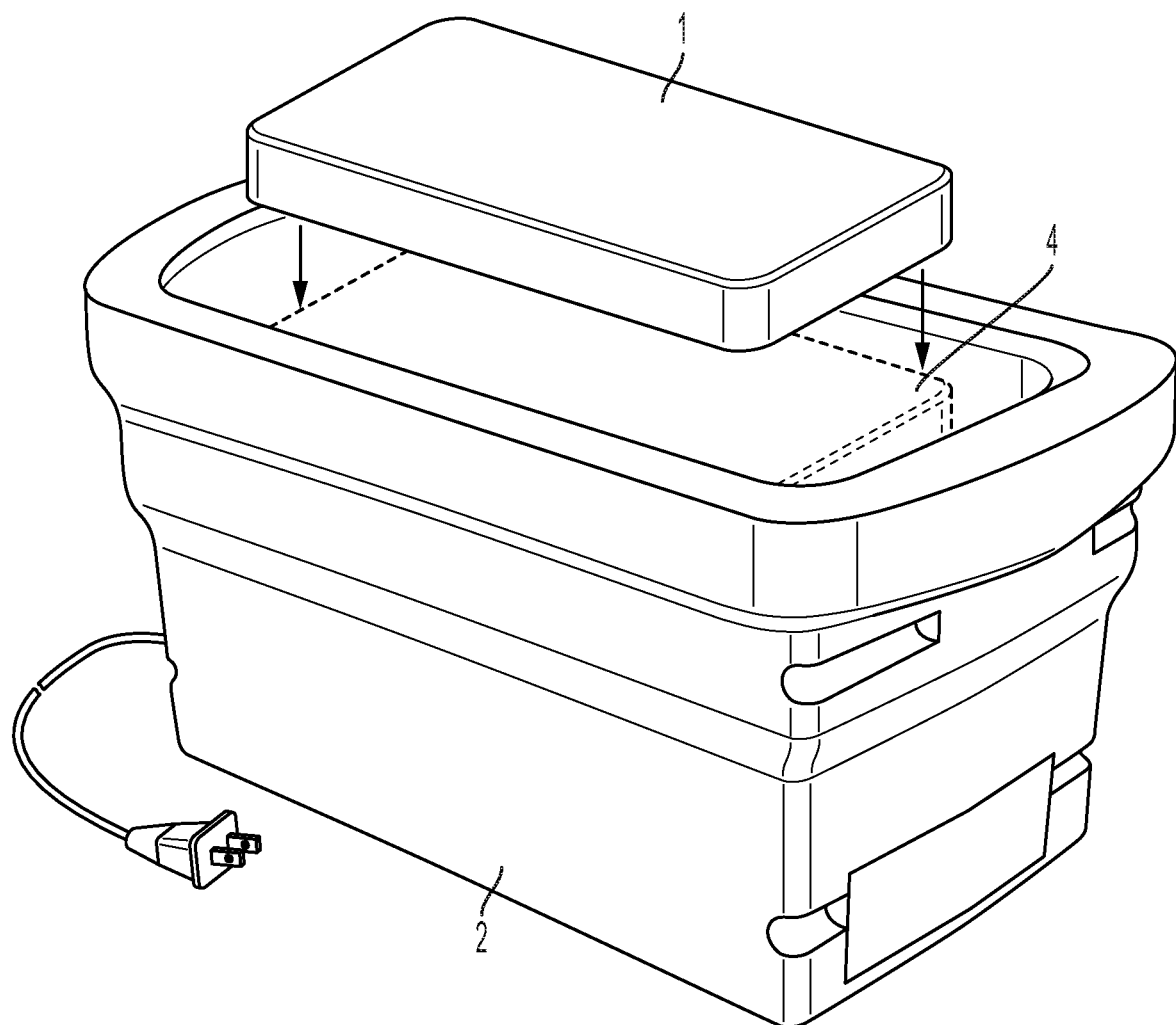
FIG. 2 shows the warmer with the solid slab being introduced into the warmer.
Figure 3:
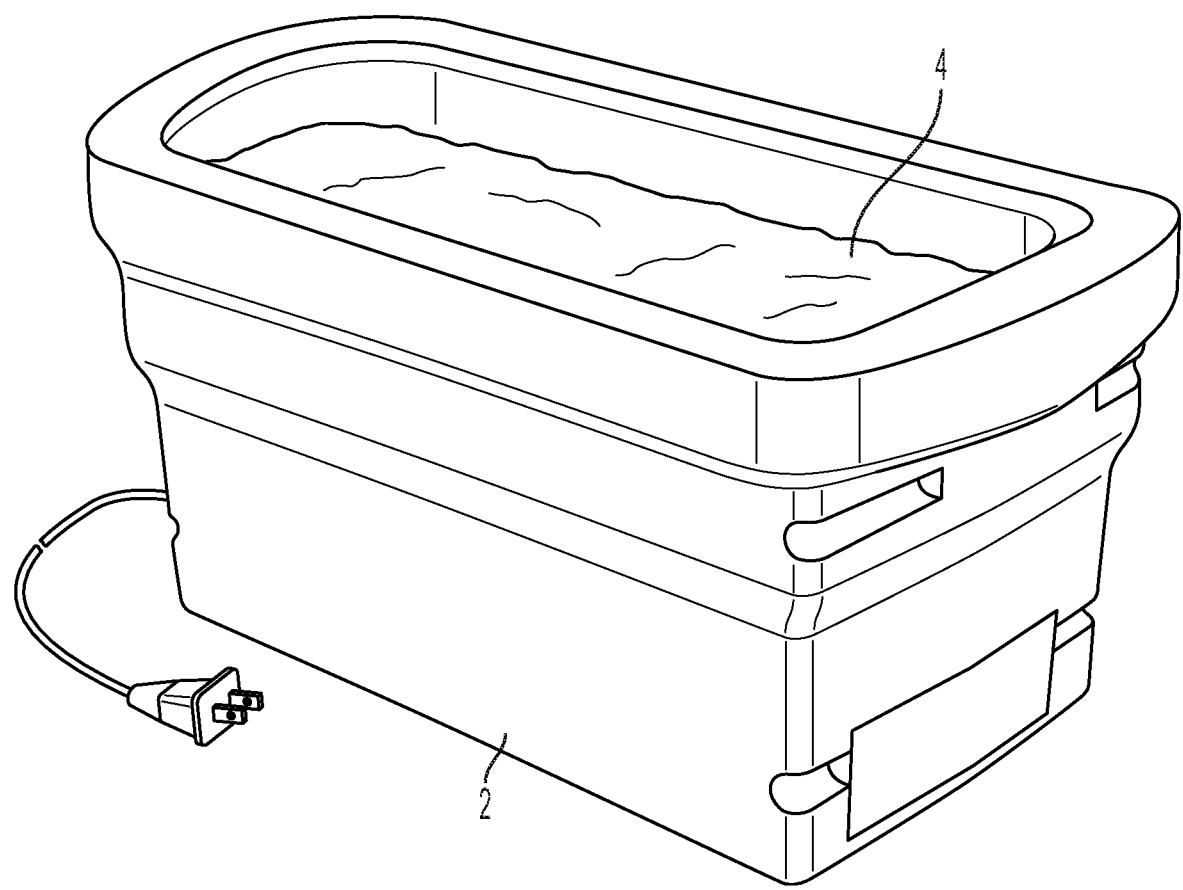
FIG. 3 shows the warmer containing the liquified slab.
Figure 4:
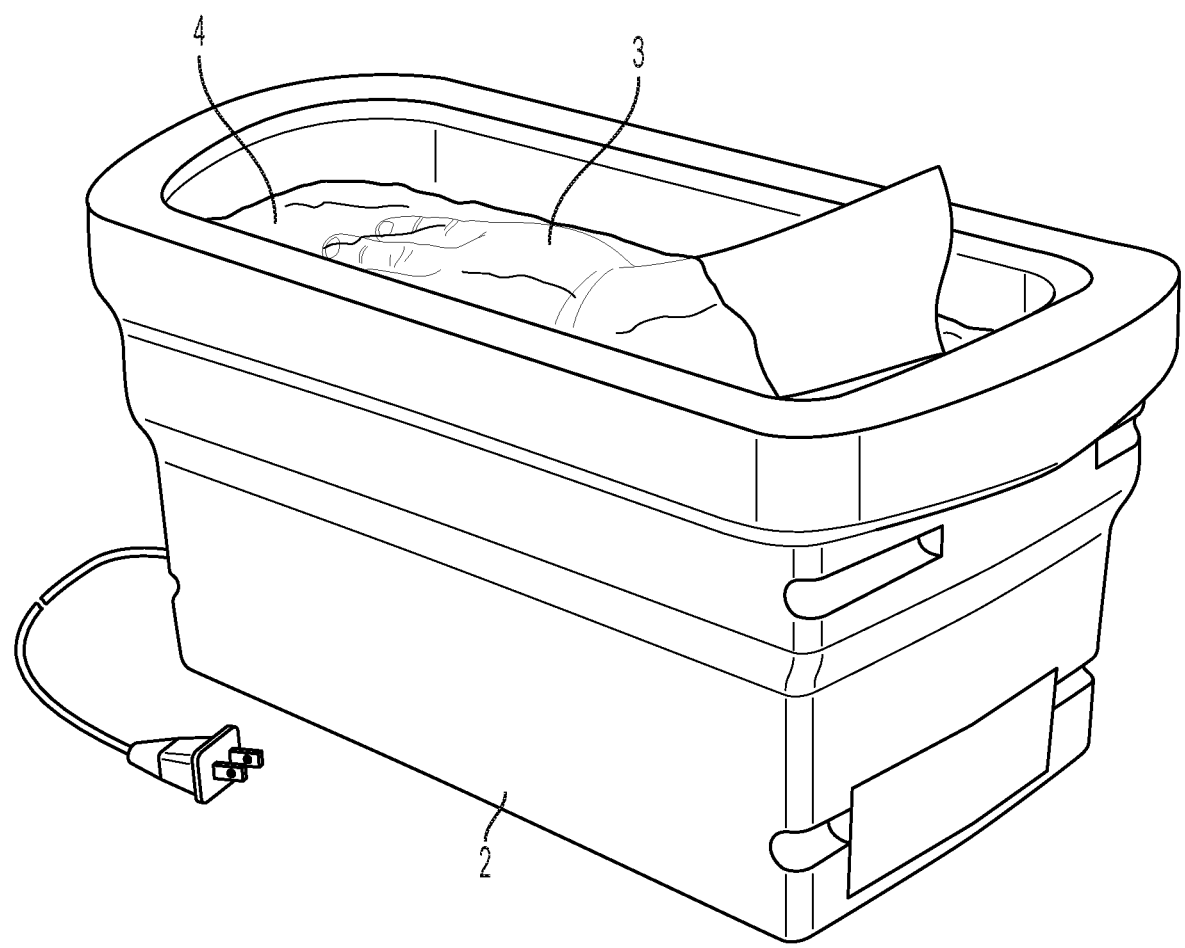
FIG. 4 shows the human subject's hand dipped into the liquified slab in the warmer.
Figure 5:
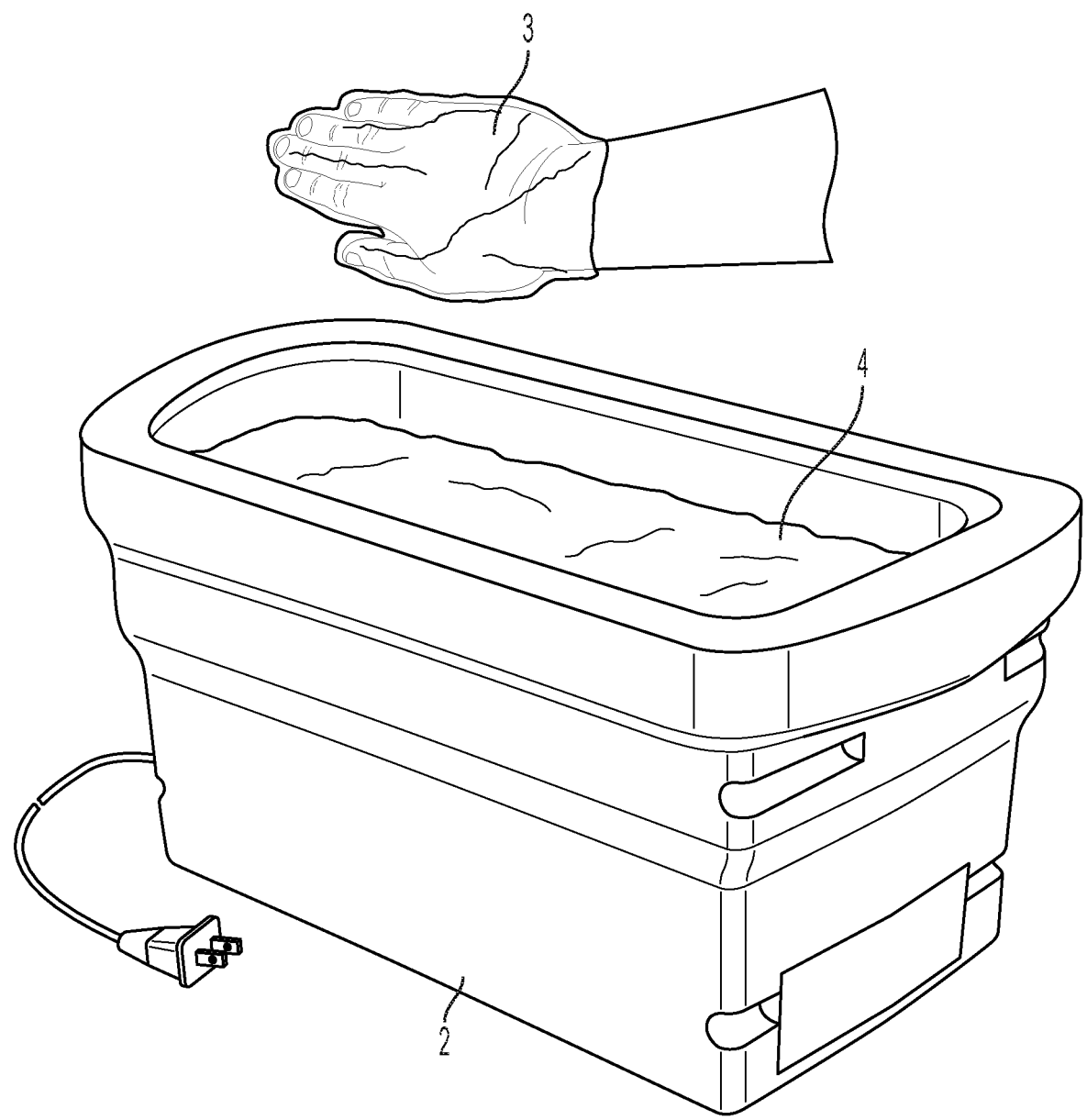
FIG. 5 shows the hand coated with wax and withdrawn from the warmer.
Figure 6:
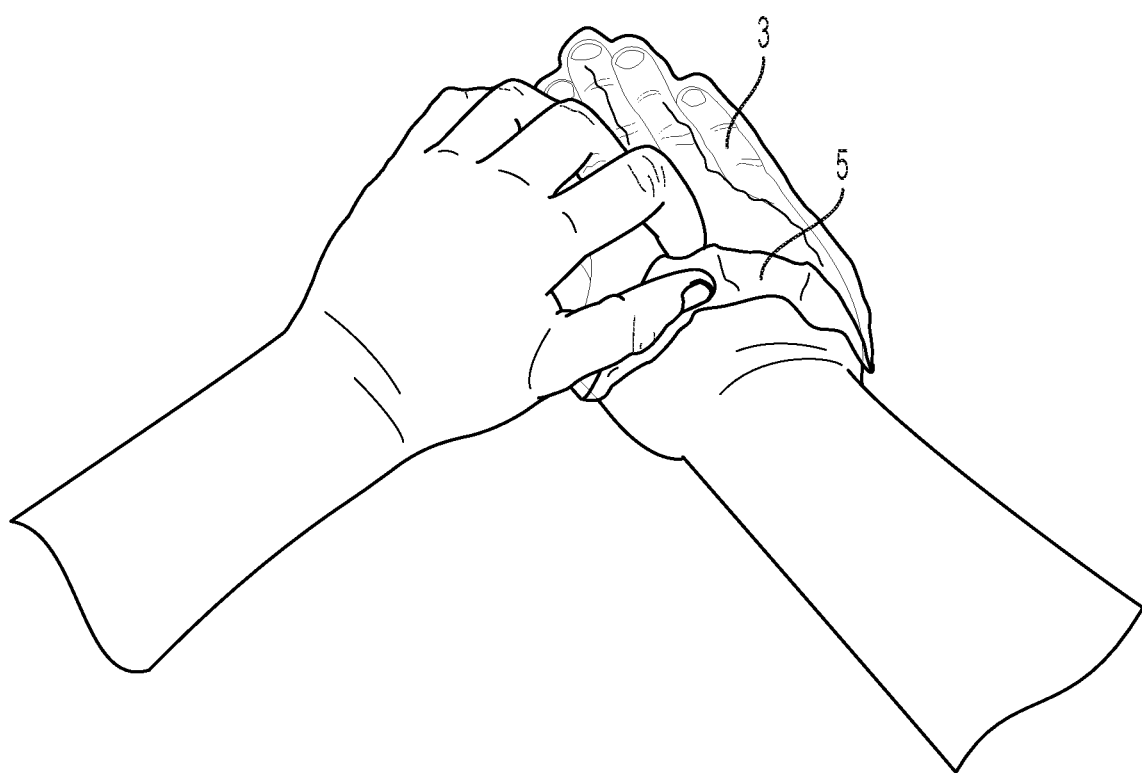
FIG. 6 shows the solidified wax being peeled off the hand.

The preferred composition of the invention is as follows:

|  | (All Percentages By Weight) |
| --- | --- |
| Paraffin wax | 91.57% |
| Mineral oil USP | 7.875% |
| Aloe vera (1x decolorized) | 0.04762% |
| Lanolin USA (extra decolorized, extra deodorized) | 0.2632% |
| Fragrance | 0.2381% |
| CBD (isolate less than 0.3% THC) | 0.0007326% |
| Benzethonium chloride USP | 0.0007326% |
| TOTAL | ~100% |

The composition of the invention is preferably made in batches which yield many slabs. The following is an illustrative batch:

| Ingredient Name | Batch | Cas No. |
| --- | --- | --- |
| Paraffin wax | 750.00 kgs | 64742-61-6 |
| Mineral oil USP | 64.50 kgs | 8042-47-5 |
| Aloe vera (1x decolorized) | 390.00 gm | 94349-62-9 |
| Lanolin USA (extra decolorized, extra deodorized) | 2156.00 gm | DOT Non-Regulated |
| Fragrance | 1950.00 gm |  |
| CBD (isolate less than 0.3% THC) | 6.00 gm | 39624-81-2 |
| Benzethonium chloride USP | 6.00 gm |  |

"Composition" as used herein is intended to encompass a product comprising the specified ingredients in the specified amounts, as well as any product that results from combination of the specified ingredients in the specified amounts.

The solid, essentially rigid slab 1, which is paraffin wax based, is heated in a warming box 2. The slab 1 is melted in the warming box, the body member 3 (hand, foot, etc.) is dipped in the warmed, liquified wax 4, preferably repeatedly, and then allowed to solidify on the body member. After cooling, the wax coating 5 is peeled off.

The method of application procedures are as follows.

Depending on the size of the warmer, the warmer usually can hold from 3 to 8 pounds which is preferred. The more of the slab in the warmer, the longer it will take to melt it. The melt time usually ranges from 1 to 3 hours in most warmers. The slab 1 starts out as a solid and melts into a liquid. The slab 1 of the invention has a melt point of 118° F. to 127° F., preferably 121° F. to 123° F., so it is hot, but not burning hot onto skin. The body member is submerged in the liquified wax at a temperature slightly above the melting point of the wax to coat the skin area to be treated.

After the slab is completely melted, the hand, foot or elbow is dipped into the warmer box quickly, preferably 5 to 6 times repeatedly. Once this is done and the coated body part exposed to the air, the melted slab begins to cool down and harden on the body part. Preferably, the solidified slab composition is left on for 15 to 20 minutes so the slab with its additives can heal or moisturize the body part. Once the time is completed, the wax has cooled and formed a hard shell, and can be peeled off slowly and discarded. Once the wax is removed, the body part will feel a bit oily. The residual oil can be wiped off with a clean towel or paper towel.

This process can be repeated several times a day or weekly if desired.

Product Identification of CBD
    Product Name
    Cannabidiol (CBD) Isolate Max.
Composition and Ingredient Information
    Chemical Identity
    Cannabidiol (CBD) 994.10 mg/gm
    CBDV 4.45 mg/gm
    THC less than 0.3% by weight
    Components
    Cannabidiol
    Synonym
    2-[1R,6R)-6-isopropenyl-3-methylcyclohex-2-en-1-yl]-5-pentylbenzene-1,3-diol
    Formula
    $C_{21}H_{30}O_2$
    Molecular Weight
    314.5
    Other
    Anhydrous powder. ~99% concentration of CBD by weight. Less than 0.3% THC. Other ingredients are other cannabinoids, terpenes and natural hemp derived plant extract. No animal-based ingredients in the isolate.
Physical and Chemical Properties of CBD
    Physical State
    Solid
    Color
    White
    Solubility in Water
    Not water soluble.
Source
    Rhizo Verified, LLC, 1942 Broadway Street, Suite 314C, Boulder, Colo. 80302.

The paraffin wax is a room temperature solid hydrocarbon having the generic formula $C_NH_{N+2}$, melting point 118° F.-127° F. The paraffin wax is fully refined with FDA status for Section 172.886 and 172.710. The other components of the slab do not significantly change the melting point.

The preferred mineral oil is Robtol 47 U.S.P. White Oil which is refined to the highest degree of purity using Vitamin E as an oxidation inhibitor. The properties of Robtol 47 U.S.P. White Oil are as shown in Table 1.

TABLE 1

| Properties of Robtol 47 U.S.P. White Oil | | | |
| --- | --- | --- | --- |
| Typical Properties | Unit | ASTM Methods | Typical |
| Viscosity @ 100 F. | SUS | D-445 | 70 |
| Flash Point | F. | D-92 | 380 |
| Saybolt Color |  | D-156 | 30 |
| Specific Gravity @ 25 | lbs/gal | LORM 046 | 0.845 |
| Pour Point | C. | D-2161 | −25 |

Preferred benezethonium chloride has a CAS No. 121-54-0. This additive is antibacterial/antimicrobial and is also known as hyamine and is a synthetic quaternany ammonium salt. It is a surfactant, antiseptic, and has anti-infective properties and is used as a topical antimicrobial agent.

Any of the well-known fragrances can optionally be used in the practice of this invention.

Depending on the size of the warmer, the warmer usually can hold from 3 to 8 pounds which is preferred. The more of the slab in a warmer, the longer it will take to melt it. The melt time usually ranges from about 1 to 3 hours in most warmers. The slab 1 starts out as a solid and melts into a liquid. The slab 1 of the invention has a melting point of about 118° F. to 127° F., preferably about 121° F. to 123° F., so it is hot, but not burning hot to the skin. The body member is repeatedly submerged in the liquified wax at a temperature slightly above the melting point of the wax.

The slab 1 can be manually handled by a technician at or around normal room or skin temperature without leaving a coating, film or residue of significant nature on the hands.

As used herein, the term "therapeutically effective amount" refers to a coating or film thickness of compositions described herein that produces therapeutic effects for which it is administered, particularly a reduction in pain or muscular or joint discomfort. This is normally carried out to produce a coating on the body member treated which is from about 0.1 mm to about 10 mm in thickness or more.

What is claimed is:

1. A composition of matter in the form of a slab comprising paraffin wax, mineral oil, aloe vera and CBD, said composition being solid, non-tacky, non-sticky and essentially non-material depositing at room temperature and at skin temperature, said composition having a melting point of about 118° F. to about 127° F.,
    wherein, at room temperature and at skin temperature, the slab does not leave a coating, film or residue on the hands.

2. A composition of matter in the form of a slab comprising paraffin wax 91.57%, mineral oil 7.875%, aloe vera (1× decolorized) 0.04762%, lanolin USA (extra decolorized) 0.2632%, fragrance 0.2381%, CBD (isolate less than 0.3% THC) 0.0007326% and benzethonium chloride USP 0.007326%, said composition being solid, non-tacky, non-sticky and essentially non-material depositing at room temperature and at skin temperature, each of the above being variable in the range 1 to 10% by weight percentages, the composition having a melting point of about 118° F. to 127° F.,
    wherein, at room temperature and at skin temperature, the slab does not leave a coating, film or residue on the hands.

* * * * *